United States Patent [19]
Rowley

[11] Patent Number: 5,958,735
[45] Date of Patent: Sep. 28, 1999

[54] POLYNUCLEOTIDES ENCODING UROGENITAL SINUS DERIVED GROWTH INHIBITORY FACTOR AND VECTORS

[75] Inventor: David R. Rowley, Houston, Tex.

[73] Assignee: Baylor College of Medicine, Houston, Tex.

[21] Appl. No.: 08/761,248

[22] Filed: Dec. 6, 1996

Related U.S. Application Data

[60] Provisional application No. 60/008,348, Dec. 7, 1995.
[51] Int. Cl.$^6$ .......................... C12N 15/18; C12N 15/63; C12N 5/10; C07K 14/475
[52] U.S. Cl. ..................... 435/69.4; 435/325; 435/243; 435/320.1; 536/23.51; 530/399; 530/834
[58] Field of Search ................................ 536/23.5, 23.51, 536/23.1; 435/69.1, 69.4, 320.1, 243, 325; 530/399, 834

[56] References Cited

U.S. PATENT DOCUMENTS

| | | | |
|---|---|---|---|
| 5,196,334 | 3/1993 | Rowley et al. | 435/240.2 |
| 5,422,262 | 6/1995 | Andersson et al. | 435/240.1 |
| 5,432,264 | 7/1995 | Grubb et al. | 530/350 |
| 5,496,800 | 3/1996 | Rowley | 514/12 |

OTHER PUBLICATIONS

Ferretti et al. Proc. Natl, Acad. Sci. 83:599–603 1986.
Hillier et al. Genbank Database Acc No. H52694 Sep. 1995.
Masahiko Tsunemi, et al. "Crystal Structure of an Elastase-Specific Inhibitor Elafin Complexed with Porcine Pancreatic Elastase Determined at 1.9 Å Resolution." *Biochemistry* 35:11570–11576 (1996).

Bryce Cowan, et al. "Elafin, a Serine Elastase Inhibitor, Attenuates Post–Cardiac Transplant Coronary Arteriopathy and Reduces Myocardial Necrosis in Rabbits After Heterotopic Cardiac Tranaplantation." *J. Clin. Invest.* 97(11):2452–2468 (Jun. 1996).

Karen Thompson, et al. "Exogenous Leukocyte and Endogenous Elastases Can Mediate Mitogenic Activity in Pulmonary Artery Smooth Muscle Cells by Release of Extracellular Matrix–Bound Basic Fibroblast Growth Factor." *Journal of Cellular PHysiology* 166:495–505 (1996).

David R. Rowley, et al. "Purification of a Novel Protein (ps20) from Urogenital Sinus Mesenchymal Cells with Growth Inhibitory Properties in Vitro*." *The Journal of Biological Chemistry* 270(37): 22058–22065 (1995).

Luca Ferretti, et al. "Total Synthesis of a gene for bovine rhodospin." *Proc. Natl. Acad. Sci. USA* 83:599–603 (1986).

*Primary Examiner*—John Ulm
*Assistant Examiner*—Christine Saoud
*Attorney, Agent, or Firm*—Conley, Rose & Tayon, P.C.

[57] ABSTRACT

Urogenital sinus derived growth inhibitory factor is a protein having growth-inhibitory and antiprotease properties. The present invention relates to amino acid and nucleotide sequences for urogenital sinus derived growth inhibitory factor.

9 Claims, 9 Drawing Sheets

FIG. 1

```
1    CGGCACGAGGAGGTCACTCGTGCAGAAGGAAAGCTGCCACCAGCCTCGGG ATG GGT AGC TGC GAC AGG AAA GCC    75
                                                         M   G   S   C   D   R   K   A     8

76   CTC TGG GCT CTG AGC TTC CTA CTG CTG CTA CTG GGC TCC AGC TCT GTT CAG GGC ACT TGG GAG GCA ATG TTG CCG   150
9    L   W   A   L   S   F   L   L   L   L   L   G   S   S   S   V   Q   G   T   W   E   A   M   L   P    33

151  GTC AGG CTG GCT GAG AAG TCC CAA GCT GAA GAG GTT GCA GCA ACA GGC TCC CGG CAG TCC CAC CAC CAG GAC CGC TGC   225
34   V   R   L   A   E   K   S   Q   A   E   E   V   A   A   T   G   S   R   Q   S   H   H   Q   D   R   C    58

226  CCA CCG CCA CCG CTA ACG CCC CTA CCC CCG GGT GCC CCG ACA CGC TGC CAG TCT GAC TCT GAG CCA CCA CCA TGC CCA   300
59   P   P   P   P   L   T   P   L   P   P   G   A   P   T   R   C   Q   S   D   S   E   P   P   P   C   P    83

301  CAC AGA CGC TGC TGT TAC AAC GGC TAT GCC TGT GTG GAG GCG GTG CCA CCA GTT CTA GAC TTA CAA GTG TTA CAA GCA   375
84   H   R   R   C   C   Y   N   G   Y   A   C   V   E   A   V   P   P   V   L   D   L   Q   V   L   Q   A    103

376  CTG GTG CAG CCC AAA CCA CGG TGG CTT CCC TGT CTG CTC TGT CCC TCA GGC TAT GAG TGC CAC ATC CTG CAG   450
104  L   V   Q   P   K   P   R   W   L   P   C   L   L   C   P   S   G   Y   E   C   H   I   L   Q    133

451  GAG GCC TGC AGC ACT GAG GAT GCC CAG GGC ATA CCC AAC CAT GGA CGG TGT GTT AAG CAA CGT CGA GCA GAG GGG CGG GTC   525
134  E   A   C   S   T   E   D   A   Q   G   I   P   N   H   G   R   C   V   K   Q   R   R   A   E   G   R   V    158

526  CCA GGG GAT GCG GCC AAG CTT CAC CAG CAG TAC CCA GAA GGT GAC TCC AAG TAT GTG GCA GAG CCT GGG AAG GGA CAA CAG   600
159  P   G   D   A   A   K   L   H   Q   Q   Y   P   E   G   D   S   K   Y   V   A   E   P   G   K   G   Q   Q    183

601  CTG CGA CAG AAG CAC TTT CCA TGA AGTGGAGACTGGCTGCCTGCCTTTGTGGGGCCTTCCACACACTACCCCTTGGAAACAGCAAAAGAATTTGACC   675
184  L   R   Q   K   H   F   P   *                                                                              208

676  AGG CAC TTT CCA TGA AGTGGAGACTGGCTGCCTGCCTTTGTGGGGCCTTCCACACACTACCCCTTGGAAACAGCAAAAGAATTTGACC   770
209  R   H   F   P   *                                                                                          212

771  CTAGACGTCAAACTCCATTCCACAGAACGGACTCCAGAGCTCCTGGGAAACGGGACTTCAGATCCCAACCCCAGAGTGGCCCAGCCTGGTGCGGCGG   866

867  TAACTTGGCtGAAGCCCTGACCACCTCTGGGTCCCGCTCAGCATCCTTGTCACAGGAACCCGCAGCTTCTAGGTGACTTTGCAGATTTTGCCTGCA   968

969  GAAGGCATATATTCATCTCTTTTTCCCCGAATAAATCTGCCCACCATGTAGCAGAAATTAAAAAAAAAAAA                             1029
```

FIG.2

```
                    58         70    75      81   87 88  92    96
PS20_RAT        CPPPPR TLPPGACQ  ATRCQSDSECPRHRRCCYNGCAYACLEAVP PPPV
ALK1_HUMAN      CPPKKS AQCLR YK  KPECQSDWQCPGKKRCCPDTCGIKCLDPVT P
CALU_CAVPD      CPRVMI YCPARH P  PNKCTSDYDCPKPQKCCPGYCGKQCYQ         PE
ELAF_HUMAN      CPIILIRCAMLN P   PNRCLKDTDCPGIKKCCEGSCGMACF    VP  Q
HE4_HUMAN       CPELQ  ADQNCT Q E  CVSDSECADNLKCCSAGCATFC           PND
IBP_TURRS       CP    K TSGPGICL H GCDSDSDCKEGQKCCFDGCGYICLTVAP SGSP
KALM_HUMAN      CPAPEK ASGFAAAC  VESCEVDNECSGVKKCCSNGCGHTCQV        PK
WAP_RAT         CPWNPIQMIAAGPCPKDNPCSIDSDCSGTMKCCKNGCIMSCMDPEPKSPTV
WDNMI_RAT       CPKNPP RSI GTCV E  LCSGDQSCPNIQKCCSNGCGHVCKSPV       F
```

FIG.8

MGSCDRKALWALSFLLLLLLGSSSVQGTWEAMLPVRLAEKSQAEEVAATGSRQPHADRCPPPPRT

LPPGACQATRCQSDSECPRHRRCCYNGCAYACLEAVPPPPVLDWLVQPKPRWLGGNGWLLDGPE

EVLQAEACSTTEDGAEPLLCPSGYECHILQPGDAAQGIPNHGRCVKQRRQAEGRVLRQKLHKEY

PEGDSKYVAEPGKGQQRHFP

MPLTGVGPGSCRRQIIRALCLLLLLLHAGSAKNIWKRALPARLAEKSRAEEAGAPGGPRQPRAD

RCPPPPRTLPPGACQAARCQADSECPRHRRCCYNGCAYACLEAVPPPPVLDWLVQPKPRWLGGN

GWLLDGPEEVLQAEACSTTEDGAEPLLCPSGYECHILSPGDVAEGIPNRGQCVKQRRQADGRIL

RHKLYKEYPEGDSKNVAEPGRGQQRHFQ

5

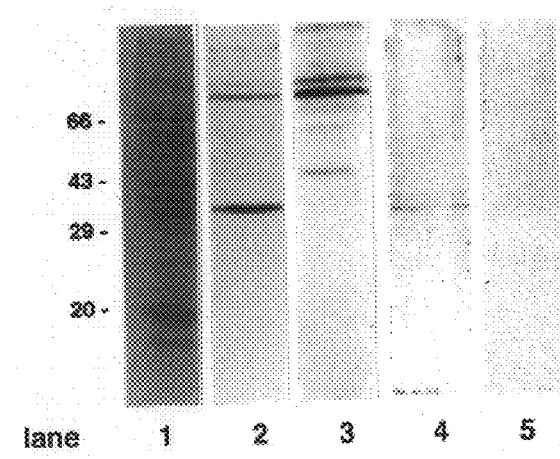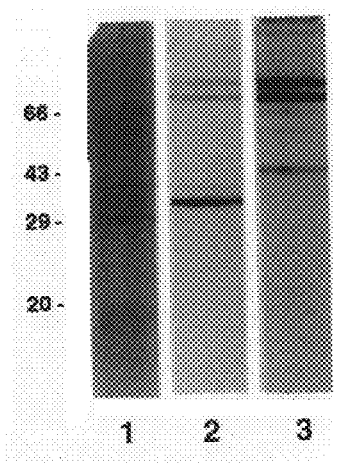
FIGURE 3A
FIGURE 3B

FIG.7

CGGCACGAGGAGGTCACTCGTGCAGAAGGAAAGCCTGCCACCAGCCTCGGGATGGGTAGCTGCG
ACAGGAAAGCCCTCTGGGCTCTGAGCTTCCTACTGCTGCTACTGGGCTCCAGCTCTGTTCAGGG
CACTTGGGAGGCAATGTTGCCGGTCAGGCTGGCTGAGAAGTCCCAAGCTGAAGAGGTTGCAGCA
ACAGGCTCCCGGCAGCCCCACGCAGACCGCTGCCCACCACCGCCACGGACGCTACCCCCGGGTG
5 CCTGTCAGGCCACACGCTGCCAGTCTGACTCTGAGTGCCCACGACACAGACGCTGCTGTTACAA
CGGCTGTGCCTATGCCTGCCTGGAGGCGGTGCCACCGCCACCAGTTCTAGACTGGCTGGTGCAG
CCCAAACCACGGTGGCTTGGTGGCAATGGCTGGCTGCTGGATGGTCCGGAGGAAGTGTTACAAG
CAGAGGCCTGCAGCACCACTGAGGATGGGGCAGAGCCACTCCTCTGTCCCTCAGGCTATGAGTG
CCACATCCTGCAGCCAGGGGATGCGGCCCAGGGCATACCCAACCATGGACGGTGTGTTAAGCAA
10 CGTCGACAAGCAGAGGGGCGGGTCCTGCGACAGAAGCTTCACAAGGAGTACCCAGAAGGTGACT
CCAAGTATGTGGCAGAGCCTGGGAAGGGACAACAGAGGCACTTTCCATGAAGTGGAGACTGGCT
GCCTTTGTGGGGCCTTTCCTGTGCTTTCCACACACTACCCCTTGGAAACAGCAAAAGAATTTGA
CCCTAGACGTCAAACTCCATTCCACAGAACGGGACTCCAGAGCTCCTGGGAAACGGGACTTCAG
ACTCCCAACCCCAGAGTGGCCCAGCCTGGTGCGGCGGTAACTTGGCGGAAGCCCCTGACCACCT
15 CTGGGTCCCCGCTCAGCATCCTTGTCACAGGAACCCGCAGCTTCTAGGTGACTTTTGCAGATTT
TGCCTGCAGAAGGCATATATTCATCTCTTTTTTTCCCCGAATAAATCTGCCCACCATGTAGCAG
AAATAAGTTCCTTTATCAGGCTCAAGTCCNAAAAAAAAAAAAAAAAAA

FIG. 9

```
   GTGCTGGACGCGGACACATGATCCGAGGGACCCTGCTGGGTGGAACTAAGAAAGTCCAGCAGAC
   TGTGCACGCTCCTGTCCCCACTCACAGGCCCACGCAGCGAGGGGGGCCCCTCTTCTGTGTGCGT
   CTGGAAGGTCGCTGCCCAGGGAGGAAATGCCTTTAACCGGCGTGGGGCCGGGCAGCTGCAGGAG
   GCAGATCATCCGGGCTCTGTGCCTCTTGCTACTTCTCCTCCACGCCGGCTCTGCCAAGAATATC
 5 TGGAAACGGGCATTGCCTGCGAGGCTGGCCGAGAAATCCCGTGCCGAGGAGGCGGGCGCGCCCG
   GCGGCCCCGGCAGCCCCGAGCAGACCGCTGCCCGCCGCCTCCGCGGACGCTGCCCCCCGGCGC
   CTGCCAGGCCGCGCGCTGTCAGGCGGACTCCGAGTGCCCGCGGCACCGGCGCTGCTGCTACAAC
   GGATGCGCCTACGCCTGCCTAGAAGCTGTGCCGCCCCGCCAGTCTTAGACTGGCTGGTGCAGC
   CGAAACCTCGATGGCTTGGTGGCAATGGCTGGCTCCTGGATGGCCCTGAGGAGGTGTTACAAGC
10 AGAGGCGTGCAGCACCACGGAGGATGGGGCCGAACCCCTGCTCTGTCCCTCGGGCTATGAGTGC
   CACATCCTGAGCCCAGGTGACGTGGCCGAAGGTATCCCCAACCGTGGGCAGTGCGTCAAGCAGC
   GCCGGCAAGCAGATGGGCGAATCCTACGACACAAACTTTACAAAGAATATCCAGAAGGTGACTC
   AAAGAATGTGGCAGAACCTGGAAGGGGACAACAGAGGCACTTTCAGTAAAGCAACGGCAAGCAG
   CTAGGTTGCAAGAACATTCCTCTACTTTCTGCTAAGCCTTGGAAACAGTTGGGAAAAGTAGTTT
15 GACCCTCACAGTTCACATTCAGCTCAGCAGAGCAAGACCCCAGAGATGCTTAGAGACAGGACAC
   CTGGCCATCAAACCCAGTTTGGCCCAGCCTGGTTGGGTGACTTTGTGGGAGCCACTTAACAGCT
   CTGGGTCCCTGTTTTACCATCCTGGGAGCAAGGCCCTGCAGCTCCACGAGACCTTTACCCCGGG
   AAGAAGCCGCCGCCCATGAAAGCATTTCTGAAGCCCCTTTCTAAGACAAGGCTCAGCATCTTGA
   TATTTTTGACAGATTCCTCCCAAGTCTGGCTCTGGGAGGTATGTACCCATCTCAAATGTTCCCA
20 AGATAAATTCATCCTTCAGGAAATGGAAATGAACTTGCTTACTAATGTGTGATTCCTAGTTGTA
   GCCACCGGATGTGCTGAGGCCTAAATGTTAGCAGGTGGGAGGAGGCCACAGAACAATAAAAACA
   ACCAAATAAAAAAAAAAAAAAA
```

FIG. 11

```
MPLTGVGPGSCRRQIIRALCLLLLLLHAGSAKNIMKRALPARLAEKSRAEEAGAPGGPRQPRADR      65
        MGSCDRKALWALSFLLLLLGSSSSVQGTWEAMLPVRLAEKSQAEE-VAATGSRQPHADR
66      78    83    89   95/96 100 104

CPPPPRTLPPGACQAARCQADSECPRHRCCYNGCAYACLEAVPPPPVLDWLVQPKPRWLGGNGW      130
CPPPPRTLPPGACQATRCQSDSECPRHRCCYNGCAYACLEAVPPPPVLDWLVQPKPRWLGGNGW

LLDGPEEVLQAEACSTTEDGAEPLLCPSGYECHILSPGDVAEGIPNRGQCVKQRRQADGRILRHK     195
LLDGPEEVLQAEACSTTEDGAEPLLCPSGYECHILQPGDAAQGIPNHGRCVKQRRQAEGRVLRQK

LYKEYPEGDSKNVAEPGRGQQRHFQ
LHKEYPEGDSKYVAEPGKGQQRHFP
```

POLYNUCLEOTIDES ENCODING UROGENITAL SINUS DERIVED GROWTH INHIBITORY FACTOR AND VECTORS

CROSS REFERENCE TO PROVISIONAL APPLICATION

This application claims the benefit of U.S. Provisional Application No. 60/008,348 filed Dec. 7, 1995.

GOVERNMENT INTEREST

The following invention was supported in part through NIH Grant Nos. DK45 909 and CA 58093. The United States Government may have certain rights in the invention.

BACKGROUND OF THE INVENTION

1. Field of the Invention

The present invention relates to a urogenital sinus derived growth inhibitory factor, ps20. More specifically, the present invention relates to uses of the factor and to the amino acid and nucleotide sequence of said factor. The present invention also relates to antibodies which bind to said factor.

2. Description of the Prior Art

Epithelial differentiation patterns are induced by stromal cells in most eukaryotic tissues including lung, breast, stomach, skin, eye, and prostate gland. In prostate development, ductal morphogenesis and epithelial acini differentiation result from stromal induction. In heterotypical tissue-tissue recombinants, mesenchyme from fetal urogenital sinus (anlagen of the prostate gland) induces bladder epithelial cells to undergo ductal morphogenesis and differentiation to a prostatic epithelial phenotype, capable of expressing prostate specific proteins.

Prostate ductal morphogenesis is characterized by a stromal-induced epithelial cell proliferation. Following this, epithelial cytodifferentiation (to the secretory phenotype) is correlated with a cellular quiescence which also requires stromal interaction. In most cells, differentiated gene expression is associated with a reduced cell proliferation. In cell culture, growth stimulatory activities (to epithelial cells) have been observed in the conditioned medium from prostate stromal cells, including bFGF and NGF-like factors. Progress has been made in the identification of keratinocyte growth factor (KGF) as a likely candidate stromal-derived factor. KGF expression is restricted to stroma and is androgen regulated in the prostate. KGF mediates in part the stromal induction of seminal vesicle epithelium proliferation. TGF-β1 and TGF-β receptors are negatively regulated by androgen in the prostate. TGF-βs are expressed in development, however, their role in prostate development is not clear. Growth inhibitory activities secreted from prostate stromal cultures have been reported by our laboratory group and others, not attributed to known inhibitory factors including the TGF-βs. This growth inhibitory activity is attributable to the urogenital derived sinus growth inhibitory factor (UGIF)/ps20 protein, which also induces protein synthesis and alters phenotypic morphology of target epithelial cells. As with all other growth regulatory proteins, ps20 is not specific to prostate, but is also expressed in mesenchymal and smooth muscle cells. The developmental pattern of prostatic ductal morphogenesis followed by epithelial differentiation likely involves the timed expression of a variety of positive and negative growth regulatory factors.

Studies with rat and human prostatic smooth muscle cell lines show androgen-stimulated proliferation with physiological concentrations (5–10 mM) of androgen. These observations together indicate urogenital sinus mesenchyme and adult smooth muscle cells likely to express genes fundamental to stromal-epithelial interactions in the prostate gland.

Progress has been limited in identification of stromal-derived regulatory proteins and their mechanisms due to technical difficulties in the isolation and culture of androgen responsive stromal cell lines, difficulties in the biochemical analysis of secreted or extracellular matrix proteins, and the relative unavailability of tissue-specific stromal cell cDNA libraries.

Benign prostatic hyperplasia (BPH) and prostate cancer are disorders of prostatic epithelial growth and differentiation. BPH disorders are perhaps most relevant to stromal-epithelial interactions. BPH initiates from localized stromal cell proliferation. The initiation of BPH has been termed a "reawakening" of the inductive potential of the prostate stroma and a spontaneous reversion of the stroma to an embryonic state. Accordingly, the abnormal proliferation of stromal cells in the periurethral region can induce the ingrowth and abnormal formation of acini from adjacent epithelial cells.

During prostate carcinogenesis, carcinoma progression patterns involve stromal-epithelial interactions. Prostatic carcinoma is typified by progression from an androgen responsive state to an androgen insensitive state which no longer responds to anti-androgen therapy. Some evidence exists to suggest that progression to androgen insensitivity results from altered gene expression in stromal cells. In the Dunning rat prostate carcinoma, the type of stroma can induce the adjacent epithelium to exhibit exon switching of FGF receptors (FGFRc2 IIIb to IIIc) which imparts androgen insensitive proliferation to these epithelial cells. Dunning tumor prostate carcinoma cell proliferation was inhibited by 7-fold when recombined with normal seminal vesicle or urogenital sinus mesenchyme. The recombined carcinoma cells showed an alteration in phenotypic morphology. When recombined with normal mesenchyme, carcinoma cells exhibited a tall, columnar cell shape, typical of a differentiated secretory epithelium as compared to the typical squamous/cuboidal undifferentiated phenotype in wild-type Dunning tumor. In this regard, it is of interest that smooth muscle is absent from Dunning prostatic tumor. In addition, the pattern of carcinoma formation can be influenced by the origin of the associated stromal cells. Recombination of bladder transitional cell carcinoma with normal urogenital sinus mesenchyme resulted in the formation of a glandular adenocarcinoma phenotype typical of prostate. Tissue-tissue recombination studies to produce prostatic tumors in mice requires transformation of mesenchyme (with myc and ras) to produce prostatic adenocarcinoma typical of the human phenotype. Conversely, the inoculation of fibrosarcoma tumorigenic stromal cells with non-tumorigenic normal epithelial cells into nude mice resulted in a mixed carcinoma-fibrosarcoma. Together these studies indicate prostatic carcinoma epithelium is responsive to the stromal environment and that progression and overall phenotype of prostate carcinoma is dependent to some degree on stromal interaction. It follows that key proteins involved in mechanisms of stromal-epithelial interactions will be of significance to the study of prostate proliferation diseases.

Balance of protease and protease inhibitor function is involved in modeling of tissues, extracellular matrix (ECM) compositions, and growth factor activation processes. Proteases play a significant role in embryogenesis, extracellular matrix modeling/remodeling and in tumorigenesis involving abnormal proliferation, promotion of tumor invasion, and formation of metastasis. It is well-established that metalloproteinases are overexpressed in most neoplastic diseases including breast cancer, colon cancer, neuroblastomas, and prostate cancer. Cysteine proteases including Cathepsins B and D are elevated in many cancer metastases, including prostate cancer. Significant to tumor progression, due to their induced cascade of effects are the plasminogen activator (PA) proteases. Plasminogen activators are serine proteases which convert inactive plasminogen to the active form, plasmin. Plasmin in turn exhibits broad proteolytic trypsin-like effects on ECM components including glycoproteins, proteoglycans (including heparin and heparin-sulfates), and gelatins. Plasmin also activates a variety of EMC bound growth factors from latent to active forms including the TGF-βs. The urokinase-type PA and tissue-type PA have been the most extensively studied PAs. Urokinase PA is primarily involved in tissue modeling-remodeling activities, whereas tissue PA is most active in blood clot lysis.

Since plasminogen is present in all tissues and fluids, local effects of plasmin are mediated by local expression of PA. Urokinase PA is secreted as an inactive pro-form which binds with high affinity to a membrane-anchored specific receptor where it is cleaved to the active form and remains (on cell surface) for several hours. On the cell surface, urokinase PA has a focal effect resulting in local acceleration of plasmin activation by approximately 40-fold. Plasmin activity is elevated in the focal environment to the cell surface expressing active urokinase. Focal plasmin effects degradation of ECM and activates metalloproteinases (procollagenases, prostromelysin, elastase). Accordingly, secretion of small amounts of urokinase PA results in a focal plasmin cascade to effect a spectrum of other enzymes and factors. Urokinase PA is inhibited by PA inhibitors (PAIs) which are serine protease inhibitors. Local actions of PAs (and other proteases) have been implicated in a wide array of developmental processes through highly regulated mechanisms. PAs, PAIs, and proteases are each regulated by hormones and growth factors.

In addition to functions in development, urokinase PA is elevated in most tumor metastases. Elevated urokinase PA leads to down stream activation of proteases and growth factors with increased tumor invasion, increased tumor volume, and increased cell proliferation rate. In the prostate, the study of proteases and inhibitors have focused primarily on carcinoma progression. PA activity is higher in prostate carcinoma than in normal tissue and the urokinase PA form is primarily associated with progression. Urokinase PA is elevated in prostate bone metastasis relative to primary tumor site. Urokinase PA is overexpressed in Dunning, Nobel, Lobund-Wistar, and Fisher-334 prostatic tumors. Moreover, urokinase PA is the predominant PA secreted by the PC-3 and DU-145 human prostatic carcinoma cell lines and these cell lines exhibit the urokinase PA cell surface receptor. Our studies have used the PC-3 cell line to identify and purify ps20 secreted from fetal urogenital sinus mesenchymal cells. Metastasis of PC-3 in nude mice was blocked by mutated urokinase PA or urokinase PA receptor blocking antibodies.

Direct evidence shows growth inhibition of cancer cells by urokinase PA inhibitors and other protease inhibitors. A synthetic urokinase PA inhibitor (p-aminobenzamidine) inhibited the progression of DU-145 human prostate carcinoma in SCID mice and cell proliferation in culture in a dose-dependent manner (64% decreased tumor volume). The protease inhibitor actinonin inhibited mammary tumor progression (both non-metastatic and metastatic types) in collagen gels. Batimastat, a matrix metalloproteinase inhibitor inhibited organ invasion in lung (72% decrease in tumor volume) of two human colon carcinomas. In human prostate, decreased expression of acid cysteine proteinase inhibitor (ACPI) (cathepsin inhibitor) was observed in BPH tissue relative to normal. No expression of ACPI was found in human prostatic adenocarcinoma tissue. Accordingly, balances of proteases and protease inhibitors likely affects proliferation in human BPH and carcinoma.

U.S. Pat. No. 5,196,334, incorporated by reference herein, describes the isolation and partial characterization of urogenital sinus derived growth inhibitory factor, UGIF (ps20). However, the amino acid and nucleotide sequence of ps20 has not heretofore been described. Additionally, antibodies to ps20 have also not heretofore been described.

SUMMARY OF THE INVENTION

The present invention relates to the amino acid and nucleotide sequences of a urogenital sinus derived growth inhibitory factor. Accordingly, provided herein is an amino acid sequence which codes for urogenital sinus derived growth inhibitory factor, UGIF (ps20). The ps20 of the present invention has protease inhibitory function. Also provided herein is a nucleotide sequence which codes for the urogenital sinus derived growth inhibitory factor protein. Also provided herein are antibodies which bind to urogenital sinus derived growth inhibiting factor, ps20.

These and other advantages of the present invention will become apparent from the following detailed description.

BRIEF DESCRIPTION OF THE DRAWINGS

FIG. 1. Rat ps20 cDNA and the deduced amino acid sequence.

FIG. 2. Alignment of four disulfide core domain of ps20 with other family members.

FIG. 3. Western analysis with ps20 peptide antibody.

FIG. 7. Sequence ID No. 1, rat ps20 cDNA nucleotide sequence.

FIG. 8. Sequence ID No. 2, rat ps20 amino acid sequence.

FIG. 9. Sequence ID No. 3, human ps20 cDNA nucleotide sequence.

FIG. 10. Sequence ID No. 4, human ps20 amino acid sequence.

FIG. 11. comparison of human ps20 amino acid sequence (top, SEQ ID NO:4) to rat ps20 amino acid sequence (bottom, SEQ ID NO:2).

DETAILED DESCRIPTION OF THE INVENTION

Figure 4A:
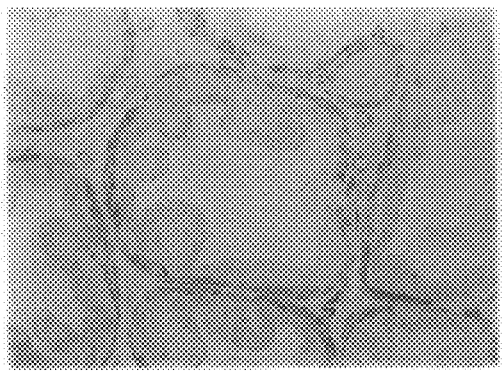
FIG. 4. Immunohistochemical localization.
Figure 4B:
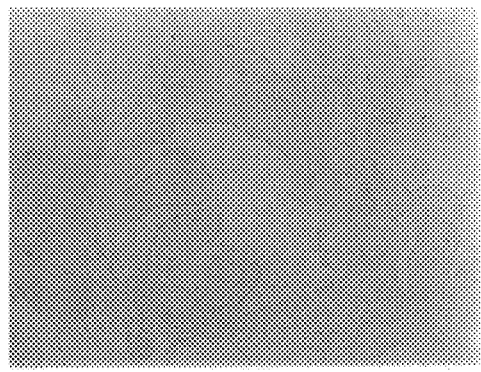
Figure 4C:
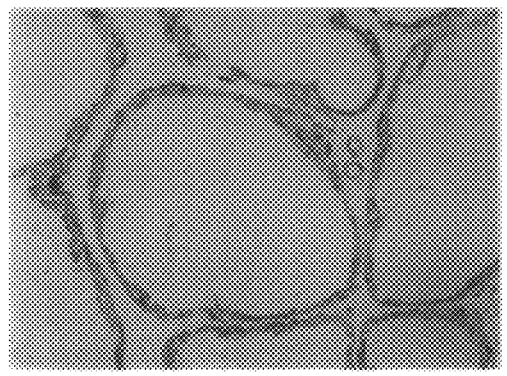
Figure 4D:
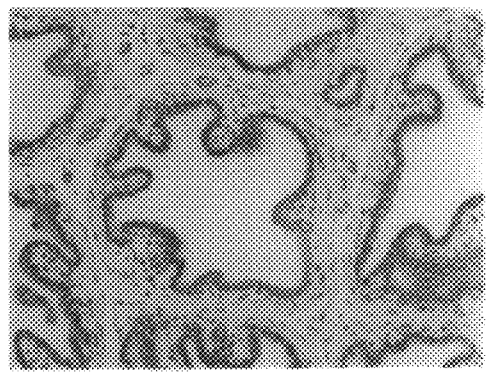

The isolation and characterization of ps20 is disclosed in U.S. Pat. No. 5,196,334, and U.S. Pat. No. 5,496,800, incorporated by reference herein. The present invention provides nucleotide and amino acid sequences of ps20. As used herein, the term "nucleotide sequence" includes polynucleotides and/or oligonucleotides and refers to a plurality of joined nucleotide units formed from naturally-occurring bases and cyclofuranosyl groups joined by native phosphodiester bonds. This term effectively refers to naturally-occurring species or synthetic species formed from naturally-occurring subunits. "Nucleotide sequence" also refers to purine and pyrimidine groups and moieties which function similarly but which have non naturally-occurring portions. Thus, nucleotide sequences may have altered sugar moieties or inter-sugar linkages. Exemplary among these are the phosphorothioate and other sulfur containing species. They may also contain altered base units or other modifications, provided that biological activity is retained. Nucleotide sequences may also include species which include at least some modified base forms. Thus, purines and pyrimidines other than those normally found in nature may be so employed. Similarly, modifications on the cyclofuranose portions of the nucleotide subunits may also occur as long as biological function is not eliminated by such modifications.

As will become apparent, cloning and sequencing of ps20 reveals that the protein has protease inhibitory function. Therefore, ps20 and its nucleotide sequence may be used in a number of applications wherein protease inhibition is desirable. These include, but are not limited to inhibition or regulation of cell proliferation, inhibition or regulation of cancer cell proliferation, inhibition or regulation of cancer metastasis, regulation of biological activities of other growth factors that are activated by protease action, regulation of extracellular matrix proteins resulting in alteration in cell proliferation and/or cell differentiation (altered gene expression) and/or cell morphologies or any other cell function regulated by extracellular matrix, activation or inactivation of growth factor activities associated with protease action. Diseases or conditions responsive to ps20 include, but are not limited to prostate cancer and metastasis, breast cancer and metastasis, ovarian cancer and metastasis, transitional cell carcinoma and metastasis, renal cell carcinoma and metastasis, bronchogenic carcinoma (lung cancer) and metastasis, colorectal carcinoma and metastasis, endometrial (uterine) carcinoma and metastasis, malignant melanoma and metastasis, hepatocellular carcinoma (kidney cancer) and metastasis, pancreatic cancer and metastasis, testicular seminomas and nonseminoma germ cell tumors and metastasis, cervical cancer and metastasis, esophageal squamous cell carcinoma and metastasis, gastric carcinoma and metastasis, atherosclerosis, restenosis after angioplasty, vascular smooth muscle proliferation associated with vascular wall injury, benign prostatic carcinoma, wound healing, and chronic inflammation. Those skilled in the art will be able to ascertain suitable doses of ps20 to achieve the desired protease inhibition function using known pharmacokinetic techniques.

Additionally, the nucleotide sequence that codes for the ps20 may be used as a diagnostic tool for assessing risk of developing prostatic diseases, such as, but not limited to, prostate cancer and benign prostatic hyperplasia. The DNA sequence coding for the ps20 may be isolated and compared to the sequence found in normal and/or at-risk individuals. In the diagnostic assay, "at-risk" individuals are those who have or may develop prostatic disease. Additionally ps20 and its nucleotide sequence can be used to prevent a number of diseases or disorders. Those skilled in the art will be able to determine appropriate preventative doses. Also, the ps20 nucleotide sequence may also be used to screen for cardiovascular diseases such as, but not limited to, arteriosclerosis and restenosis. The nucleotide sequence of the present invention may be used to construct recombinant proteins having the amino acid sequence of rat or human ps20. Additionally, proteins having minor modifications may also be constructed using the nucleotide sequence of the present invention. Also provided are vectors comprising the nucleotide sequence of the present invention.

Also provided herein are antibodies to ps20. The antibodies can be used to identify and enumerate ps20-bearing cells, or can be used to isolate or quantitate the amount of ps20 in body fluids. For this purpose, antibodies can be used in standard assays known to those skilled in the art. In general, antibody is contacted with a sample under conditions which allow the antibody to bind ps20 . Quantitation is conducted by conventional techniques known to those skilled in the art. These include, but are not limited to histochemical techniques EMIT, ELISA, latex agglutination immunoassays, FPIA and other immunoassay techniques useful antibodies to ps20 include polyclonal or monoclonal antibodies.

The following examples serve to illustrate specific embodiments of the invention, but should not be considered as a limitation on the scope of the invention.

EXAMPLE 1

Cloning and sequencing of ps20

This example describes the cloning and nucleotide sequence of rat ps20. To clone ps20 cDNA, a cDNA library was prepared from the rat prostate smooth muscle PS-1 cell line, which was a high expressor of ps20 as determined by Western analysis. The PS-1 cell line is described in U.S. Application, Ser. No. 07/928,867 now U.S. Pat. No. 5,496, 800. The cDNA library was constructed in lambda ZAP Express vector from oligo d(T) primed cDNA. The ZAP Express vector was chosen based on versatility, ease of excision and recircularization to produce pBK-CMV phagemid subclones. The library exhibited anticipated representation of B-actin cDNA (as control) and IgG lectin-binding protein cDNA in test screening.

As an initial approach, degenerate primers were prepared based on the 5' ends of the amino terminal sequence as determined from purified ps20 protein. Due to degeneracy of PCR probes, a nested PCR approach amplifying from 5' vector primer to a ps20 degenerate primer followed by a nested amplification using ps20 forward and reverse degenerate primers allowed for amplification of authentic ps20 sequence (amino terminal end). The final PCR product had a predicted size of 81 bp, was cloned directly into pCR II plasmid by TA cloning, clones isolated, and clone 3438pCRII sequenced. The corresponding sequence was confirmed as ps20 by a direct match of the deduced amino acid sequence with the amino terminal sequence determined from purified ps20. Non-degenerate forward and reverse PCR primers were developed based on clone 3438pCRII sequence, and used in nested PCR reactions to amplify and clone the 3' and 5' ends of ps20 cDNA. The 5' clone (clone T340pCRII) was 184 bp, and overlapped (by 50 bp) with clone 3438pCRII sequence plus an additional 120 bp of 5' sequence. The 3' clone (clone 42T7pCRII) was 868 bp in length, contained a 3' poly A tail, and overlapped (by 54 pb) with clone 3438pCRII sequence.

Screening of PS-1 cDNA library was based on PCR to score positive plates followed by plaque hybridization with clone 42T7pCRII labeled insert (862 bp) as a probe to score individual colonies. A total of 1.2 million clones were screened with one positive clone detected in every 10–20, 000 colonies. Clone 1025rps20pBK-CMV-1B was sequenced from both directions (sequence shown in FIG. 1), matched sequence from an additional separate clone 1025rps20pBK-CMV-2B, and confirmed as ps20 by deduced amino acid sequence identical to native ps20. Clone 1025rps20pBK-CMV-1B was 1029 bp in length and contained a 3' poly (A) tail in agreement with Northern analysis of U4F cells and rat dorsolateral prostate which showed a single, identical sized species at approximately 1.1 kb as shown in FIG. 1. Sequence analysis indicated an open reading frame of 636 nucleotides beginning at nucleotide 52 (ATG), ending at nucleotide 688 (UGA stop codon), and coding for a deduced 212 amino acid protein. A hydrophobic leader sequence was predicted for amino acid 1-26 with a perfect signal peptidase cleavage site between Gly (#26) and Thr (#27) (−1 and +1 respectively) following the rules of von Heijne. Von Heijne, G. 1984. *How signal sequences maintain cleavage specificity. J Mol. Biol* 1 73:243–251. Thr (#27) (position +1 of mature secreted protein) through His (#54) were an exact match with Thr (#1) through His (#28) determined from the amino terminal of purified native ps20. Hydopathy analysis (Tmpred) suggested no transmembrane domain, predicting a secreted protein. No potential post-translational modifications were indicated with the exceptions of 5 potential casein kinase II sites. The cDNA clone predicts a mature, secreted protein of 20.7 kDa (identical to purified native 21kDa ps20) and an intracellular molecular weight of approximately 23.6 kDa (including hydrophobic signal peptide) in close agreement with detection by Western analysis indicating an intracellular Mr of 29 kDa under these conditions.

Using clone 1025rps20pBK-CMV-2B as a labeled probe, a lambda gt11 library prepared from normal human prostate gland (human prostate 5'-STRETCH cDNA, Clontech) was screened (1.2 million clones) with standard plaque hybridization techniques. Eight clones were isolated as potential full length, based on PCR screening of 5' and 3' ends. Of these, 5 were likely full length (1–1.2 kb) based on comparison to rat ps20 cDNA and the previous determination of human ps20 protein exhibiting an identical molecular weight to rat ps20.

The nucleotide sequence of rat ps20 is shown in FIG. 1 (SEQ ID NO 5). Additionally, FIG. 7 depicts the nucleotide sequence of rat ps20 and which is referred to herein as Sequence ID No. 1. The sequence of FIG. 7 contains extra nucleotides in the 3' uncoding region which is not depicted in the sequence shown in FIG. 1. Also shown in FIG. 1 is the deduced amino acid sequence of rat ps20 (SEQ ID NO. 6). The rat ps20 amino acid sequence is also shown in FIG. 8 and is referred to herein as Sequence ID No. 2. The underlined portion represents a signal peptide (amino acids 1–26). The ps20 protein is encoded by a single 1.1 kb transcript expressed in U4F mesenchymal cell cultures and rat adult prostate tissue. The transcript codes for a 23.6 kDa protein having a predicted signal peptide leader sequence (aa 1–26) with a prototypical signal peptidase cleavage site prior to the first amino acid of the secreted purified protein.

Analysis of deduced amino acid sequence revealed that ps20 has a WAP-type four disulfide core domain, classifying ps20 as a novel member of the WAP-type four disulfide core domain protein family. Cysteines 58–96 which participate in the WAP --type four disulfide core domain are also underlined in FIG. 1. The members of the WAP-type four disulfide core domain family are relatively small proteins containing a conserved 8 cysteine motif in the protein core involved in disulfide bonds. The majority of family members with known biological activity function as protease inhibitors. The family members having core domains most closely related to ps20 include: Chelonianin, 39.4% identity to ps20 (subtilisin protease inhibitor isolated from red sea turtle egg white); Antileukoproteinase 1, 35.4% identity to ps20 (HUSI-1, a secreted serine protease inhibitor); WAP, 35.3% identity to ps20 (whey acidic protein, a suspected protease inhibitor found in milk); WDNM1 protein, 33.3% identity to ps20 (a mammary gland metastasis-suppressor gene with predicted protease inhibitor function); HE4, 33.3% identity to ps20 (a predicted protease inhibitor secreted into epididymis); Kallman syndrome protein, 31.2% identity to ps20 (predicted protease inhibitor localized in extracellular matrix and required for proper olfactory and GnRH-synthesizing neuronal development); Elafin, 29.2% identity to ps20 (a secreted elastase-specific serine protease inhibitor); and Caltrin-like protein II, 27.1% identity to ps20 (a secreted protein from seminal vesicle inhibiting calcium transport into spermatozoa). FIG. 2 depicts the alignment of four disulfide core domain of ps20 with other family members (1. SEQ ID NO. 7; 2. SEQ ID NO. 8; 3. SEQ ID NO. 9; 4. SEQ ID NO. 10; 5. SEQ ID NO. 11; 6. SEQ ID NO. 12; 7. SEQ ID NO. 13; 8. SEQ ID NO. 14; 9. SEQ ID NO. 15). Alignment scores were computed by a fasta scoring method. (EERIE).

Functional significance of this protein family points to roles in tissue modeling, cell differentiation and cancer metastasis control. WAP may play a role in terminal differentiation and development of mammary acinar epithelial cells. Directed expression of a WAP transgene by MMTV has resulted in impaired mammary gland development and a hyperplasia/dysplasia of the coagulating gland (anterior prostate gland) in male reproductive tract. This observation is of significance since it was observed that there was an increased staining intensity of ps20 in human BPH as compared to normal human prostate tissue.

Kallman syndrome produces an agenesis of olfactory bulbs referred to as "olfactogenital dysplasia" and a hypogonadotropic hypogonadism. The defective gene in Kallman syndrome is termed ADMLX and encodes a secreted protein containing the WAP-type four-disulfide core domain as well as fibronectin type III repeats. This protein may function in cell adhesion and as a protease inhibitor. ADMLX may participate in migration of GnRH neurons and the axonal extension of olfactory neurons, thereby inducing a differentiation pattern.

The WDNM1 gene is novel member of the four disulfide core protein family with proposed metastasis-suppressor functions. WDNM1 is down-regulated by 20-fold in rat metastatic mammary adenocarcinoma in comparison to non-metastatic mammary carcinomas. WDNM1 has been suggested to function as a protease inhibitor and hence, modulation of WDNM1 protein could result in unregulated protease activity, commonly associated with metastatic spread of carcinomas.

EXAMPLE 2

Preparation of Antibodies to ps20

This example describes the preparation and characterization of antibodies specific to ps20. ps20 in rat and human tissues was localized with immunohistochemistry. A synthetic peptide was made based on positions 1–14 of ps20 peptide sequence and used as immunogen in female New Zealand rabbits following modifications of the procedures of Vitukiatis. Vitukaitis, J, J. B. Robbins, E. Nieschlag, and G. T. Ross. 1971. *A method for producing specific antisera with small does of immunogen. J. Clin. Endocr.* 33: 988–991.

A 14 amino acid synthetic peptide corresponding to and unique to the amino terminus of purified ps20 was synthesized on an Applied Biosystems 430A Peptide Synthesizer: N-Thr-Trp-Glu-Ala-Met-Leu-Pro-Val-Arg-Leu-Ala-Glu-Lys-Ser-C. For initial immunization, ps20 peptide was solubilized in sterile, tissue culture grade $H_2O$ (400 µg/ml) and mixed with Freund's complete adjuvant (1:1 ratio) and injected in 500 ml (100 µg) aliquots at multiple sites (4–5) in the neck (subcutaneous) and in the subscapular muscle tissue in the back (intramusclular) of three female New Zealand rabbits. At three weeks post primary immunization, sera samples were prepared and analyzed by solid phase enzyme linked immunoabsorbance assay (ELISA). Each antibody positive rabbit received a booster of 100 µg peptide in 500 µl of Freund's incomplete adjuvant injected subcutaneously into multiple sites of the back and neck, and an additional 100 µg intramusclular in the subscapular region. Serum samples were tested for ps20-specific antibody every 2 weeks and immunoglobulin subtype determined by ELISA analysis. Sera was tested for ps20 antibody at three weeks following the initial booster and antibody positive rabbits received a secondary booster following identical procedures. Sera from rabbits producing high titer antisera (activity at 1:106 dilution) was pooled and IgG was precipitated by ammonium sulfate (50% saturation), resolubilized in PBS, and dialyzed overnight against PBS at 4° C. The specificity of the antibody was confirmed by immunoreactivity with a 20 kDa protein in concentrated, partially purified preparations of conditioned medium from U4F cells, from which ps20 was purified.

Immunoreactive IgG was purified by peptide column chromatography. Peptide (10 mg) corresponding to the first 14 amino acids of purified ps20 was generated as described above, and coupled to 1 g CNBr-activated Sepharose 4B following standard procedures as described in *Methods in Molecular Biology*, Vol. 34, "Immunocytochemical Methods and Protocols", Lorette C. Javois (ed.), Chapters 19–23, pgs. 155–193, Humana Press, Totowa, N.J. 1994 and poured into a 2 ml Poly-Prep column (Bio Rad). IgG preparations were diluted in PBS buffer (200 mM sodium borate, 160 mM sodium chloride, pH 8.0) and chromatographed through the column two times sequentially. The column was washed extensively in PBS (10–15 column volumes) and bound antibodies eluted with glycine-Cl buffer (0.05 M glycine, 0.15 M NaCl, pH 2.28). Fractions (2 ml) were eluted and collected directly in tubes containing 0.5 ml neutralizing buffer (0.5M phosphate, pH 7.7). Fractions were assayed for protein content (absorbance at 280 nm) and peak fractions pooled and assayed for immunoreactivity by solid phase enzyme linked immunoabsorbance (ELISA) assay. Antibody production was scored by ELISA. High titer antisera was detected in 3 rabbits.

An IgG fraction of ps20 antisera was analyzed for specificity by Western analysis and affinity purified antibody prepared by gel chromatography using peptide 1–14 covalently attached to sepharose 4B. Western analysis indicated mono-specific reactivity with the ps20 (20-21 kDa) secreted form (minus signal peptide) in conditioned medium. See, Rowley, D. R., T. D. Dang, M Larsen, J. J. Gerdes, L. McBride, and B. Lu. 1995. *Purification of a novel protein (ps20) from urogenital sinus mesenchymal cells with growth inhibitory properties in vitro*. J Biol. Chem. 270: 22058–22065. Western analysis from U4F cell extracts showed mono-specific reactivity with a 29 kDa protein (FIG. 3) representing the unprocessed cellular form (includes a 26 amino acid hydrophobic leader sequence) predicted to increase the apparent backbone (24.6 kDa) size in SDS-PAGE and Western analysis. (A) U4F fetal rat urogenital sinus mesenchymal cells. Lane 1: Coomasie stain, 2: ps20 antisera IgG fraction, 3: preimmune sera, 4: affinity purified ps20 antibody, 5: no primary antibody. The ps20 antisera IgG fraction (lane 2) specifically recognized a single species of apparent 29 kDa size under these conditions. The affinity purified antibody (lane 4) recognized the 29 kDa band exclusively. Preimmune sera (lane 3) recognized all non-specific cross-reactive bands. Secondary antibody alone showed no banding pattern (lane 5). Western analysis of adult rat prostate smooth muscle and human prostate smooth muscle extracts showed identical immunoreactivity to a 29 kDa band from both rat and human cell lines. These studies indicated rat and human ps20 forms were identical in size and immunoreactivity as predicted by nearly identical amino acid sequence.

EXAMPLE 3

Immunohistochemical Localization

This example shows the immunohistochemical localization of ps20 in prostate specimens.

Figure 4E:
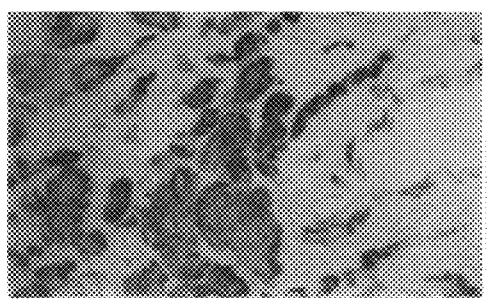
Figure 4F:
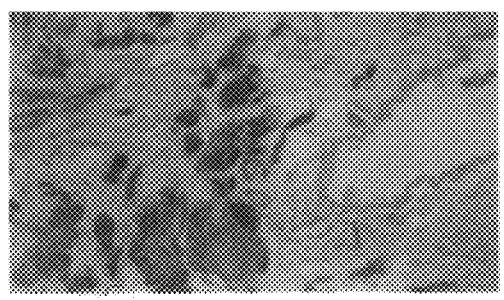
Figure 5A:
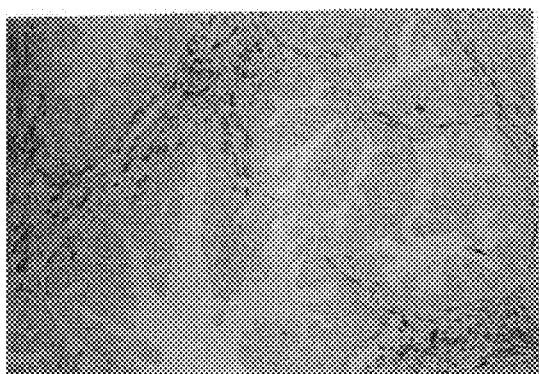
FIG. 5. Immunolocalization of ps20 in human benign prostatic hyperplasia.
Figure 5B:
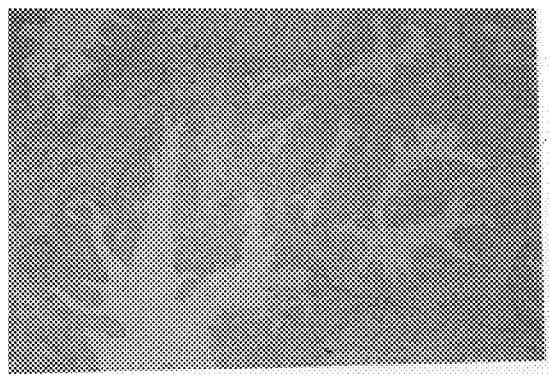
Figure 5C:
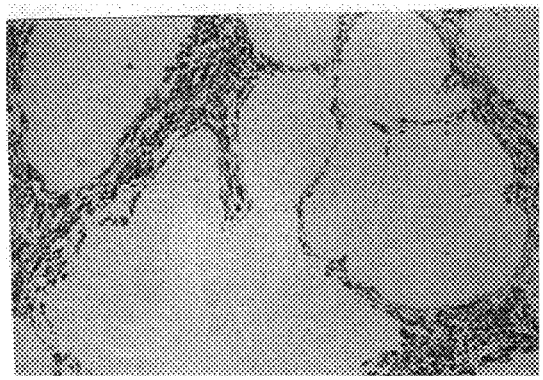
Figure 5D:
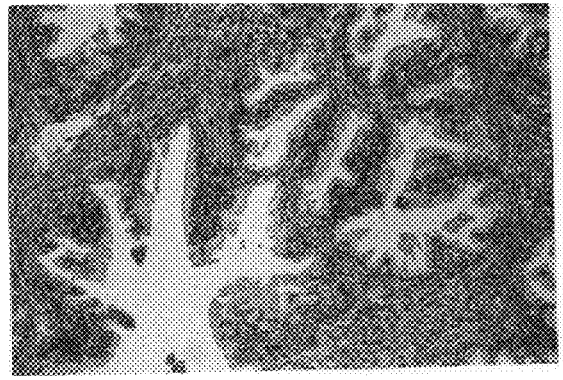
Figure 6A:
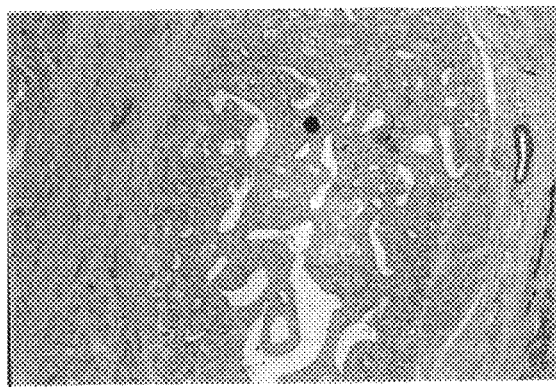
FIG. 6. Immunolocalization of ps20 in human poorly differentiated carcinoma.
Figure 6B:
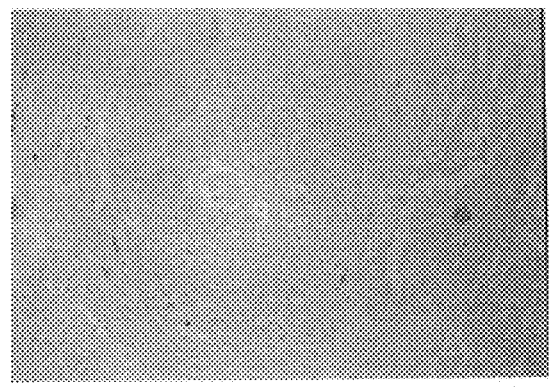
Figure 6C:
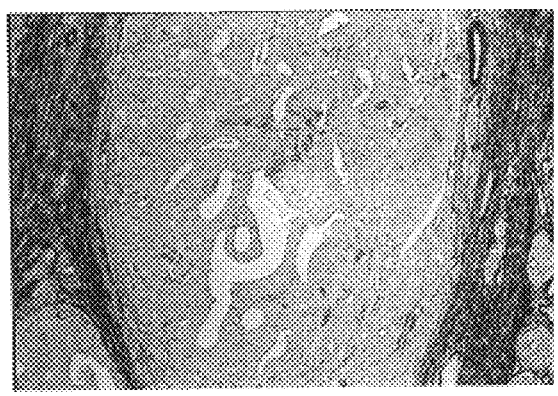
Figure 6D:
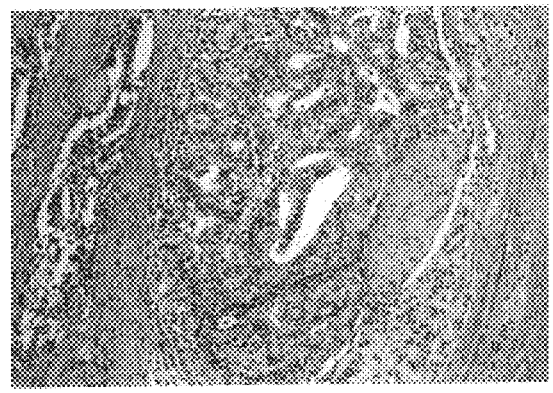

FIGS. 4E & F, 5, and 6 show ps20 localization in human prostate specimens. FIG. 4 shows ps20 immunohistochemical localization in rat prostate gland with affinity purified antibody. Immunohistochemical localization was conducted by the procedure described in *Methods in Molecular Biology*, Vol.34, "Immunocytochemical Methods and Protocols", Lorette C. Javois (ed.), Chapters 19–23, pgs. 155–193, Humana Press, Totowa, N.J. 1994. Basically, two month old and six month old male Sprague Dawley rats ( ) were sacrificed and whole tissues fixed in formalin O.N. Fixed tissues were embedded in paraffin and cut into 5 µm thick sections that were applied to poly-L-lysine coated slides and baked at 37C prior to staining.

Formalin-fixed, paraffin-embedded sections of human prostate gland from 31 patients were obtained from Methodist Hospital, Houston (18), and from Texas Children's Hospital, Houston (13). Sections of 5µm thickness were cut from the paraffin embedded blocks and applied to poly-L-lysine coated slides. Slides from twenty four adult patients ages 53 to 72 generally characterized as: carcinoma (9), BPH (3), severe BPH (2), stromal BPH (3), and normal (6) were stained for ps20. Slides from four patients of less than one year of age and four patients with ages between 10–14 years were stained.

Tissue sections were deparaffinized by immersion in Hemo D 1×10 min. and 1×5 min.; rehydrated by 5 min. graded washes in 100%, 95%, and 70% ethanol; permeablized by immersion in 1×PBS/0.1% Triton-X-100 for 5 min.; and treated 5 min. with 3% peroxide ($H_2O_2$) (diluted from 30% Sigma) to minimize endogenous peroxidase activity. Primary antibody incubations were performed at the concentrations and conditions described for immunocytochemistry, with the exception that affinity purified ps20 antibody was incubated with tissue sections O.N. at 37° C. Immunoreactivity was visualized by a 45 min. incubation with either biotinylated goat anti-rabbit or goat anti-mouse secondary antibodies (Sigma), diluted 1:15; followed by a 30 min. incubation with ExtrAvidin-conjugated peroxidase (Sigma), diluted 1:15; concluding with a 7 min. incubation with diaminobenzidine (DAB) and mounting with Gel Mount. Staining of slides with hemotoxalin and eosin (H & E) were performed as described in *Methods in Molecular Biology*, Vol. 34, "Immunocytochemical Methods and Protocols", Lorette C. Javois (ed.), Chapters 19–23, pgs. 155–193, Humana Press, Totowa, N.J. 1994. Slides were analyzed by light microscopy (Labophot-2, Nikon) and photographed on Ectachrome 400 slide or Royal Gold 25 print film (Eastman Kodak).

In FIG. 4, Panel (A) depicts the affinity purified ps20 antibody, Panel (B) the negative control, Panel (C) the smooth muscle a-actin (SM aactin), and Panel (D) hematoxylin and eosin staining patterns. ps20 antisera (A) and the ps20 IgG fraction showed the same specific immunolocalization in rat prostate periacinar smooth muscle. Negative controls, including no primary antibody (B), preimmune sera, and antibody preabsorbed with ps20 peptide, showed the same lack of specific staining. ps20 immunolocalized to a subset of SM a-actin positive cells. Immunolocalization is specific to smooth muscle, but is not specific to prostate. Strong staining was observed in the smooth muscle of other male reproductive tract tissues, including the vas deferens and seminal vesicle. Moderate staining was observed in the tunica media of arteries and the smooth muscle of colon and small intestine. No apparent staining was observed in the brain, lung, bladder, or testis. Immunolocalization of ps20 in human prostate Panel (E) showed a localization corresponding to a subset of SM a-actin positive cells as shown in Panel (F). Exclusive localization was observed in the periacinar smooth muscle cells immediately adjacent to epithelial acini. Significant reactivity was not observed in any other cell type. A survey of other tissues including seminal vesicle, vas deferens, stomach, intestine, lung, salivary gland, heart, brain and testis showed ps20 expression exclusive to smooth muscle. Highest reactivity was noted in male reproductive tract tissues (vas deferens, prostate, seminal vesicle) with moderate staining in smooth muscle of gut and tunica media of arteries. No reactivity was noted in testis, lung, or brain. Of interest, ps20 reactivity was observed in the tunica media of arteries in the prostate gland. Localization was specific to smooth muscle cells ($\alpha$-actin positive stromal cells). The human, unlike rat, does not have a precise periacinar ring of smooth muscle cells around epithelial acini. Rather, human prostate stroma is a mix of smooth muscle and fibroblasts. The ps20 positive cells correlated with $\alpha$-actin positive cells all sections. Of interest were the staining patterns observed in prostatic disease.

FIG. 5 and 6 show ps20 localization in BPH and prostatic carcinoma consistently high relative to normal. In FIG. 5, Panel (A) depicts ps20 antisera IgG fraction, Panel (B) preimmune sera, Panel (C) SM a-actin, Panel (D) hematoxylin and eosin staining. Immunolocalization of ps20 in regions of BPH is similar to that in normal regions of the adult human prostate or is slightly elevated in comparison to normal. Strong to elevated staining was observed in patients having both glandular and stromal BPH. The staining pattern shown here is representative of sample evaluated (5 patients diagnosed with glandular BPH and 3 with stromal BPH.) In contrast, staining intensity of ps20 was very heterogeneous and generally lower in carcinoma samples. In FIG. 6, Panel (A) depicts ps20 antisera IgG fraction, Panel (B) preimmune sera, Panel (C) SM a-actin, Panel (D) hemtoxylin and eosin staining. Immunolocalization of ps20 in regions of carcinoma exhibited a heterogeneous staining pattern relative to normal in nine carcinoma patients evaluated. ps20 staining was reduced in stroma surrounding some poorly differentiated nodules, as shown in Panel (B). In particular, ps20 staining intensity was low or absent altogether in some (not all) stromal regions adjacent to poorly differentiated carcinoma nodule located in the peripheral, subcapsular region as shown in FIG. 6.

EXAMPLE 4

Human ps20 sequence

This example describes the nucleotide and deduced amino acid sequence of human ps20. A commercially available (Clonetech, Palo Alto, Calif.) cDNA library was used. The library was prepared from normal human prostate gland. Screening was done using standard plaque hybridization procedures as described in *Current Protocols in Molecular Biology*, Vol. 1, Ausubel, F. M.; Brent, R.; Kingston, R. E.; Moore, D. D; Seidman, J. G.; Struhl, K.; and Smith, J. A. (eds.), John Wiley & Sons, NY, N.Y. 1995. Plaques were transferred to Nytran 0.45 $\mu$m membranes (Schleicher and Schuell, Keene, N.H.), DNA cross linked by the Stratalinker UV cross linker (Stratagene), and membranes prehybridized 2 h in at 42° C. in the hybridization solution (50% formamide, 2×PIPES buffer, 0.5% (w/v) SDS, 100 $\mu$g/ml sonicated salmon sperm DNA). Clone 42T7pCRII insert was purified from an agarose gel slice by Spin-X columns (Corning Costar Corp., Cambridge, Mass.), 150 ng labeled with $\alpha[^{32}P]$-dCTP (Amersham, Cleveland, Ohio) by random priming with Klenow Enzyme (labeling grade, Boehringer, Mannehiem, Indianapolis, Ind.). Unicorporated nucleotides were removed by NucTrap Probe Purification Column (Stratagene), and denatured probe hybridized with filters at 1 -3×10$^6$ counts/ml overnight at 42° C. in hybridization cocktail. Filters were washed 3×10 min at room temperature in 2×SSC, 0.1% SDS, and 2×20 min at 55° C. in 0.2×SSC, 0.1% SDS and exposed to X-OMAT AR film (Eastman Kodak, Rochester, N.Y.). Positive plaques were screened by PCR, phagemids excised from lambda arms by the Rapid Excision Kit (Stratagene), and DNA prepared either by mini alkaline lysis or by Oiagen tip-500 (Oiagen, Chatsworth, Calif.) The probe was rat ps20 cDNA clones labeled with $^{32}P$. Colonies of DNA were lifted via filters and hybridized to the rat ps20 cDNA clones. Positive colonies were selected and purified by second and third round screening.

Positive colonies were sequenced and compared to the rat sequence. Positive clones $H_1T_2100$ and $H_6B_2$-3 were sequenced using both dideoxy sequencing (as described in Current Protocols in Molecular Biology Vol 1, see above) and automated sequencing using the IBI model 377 automated sequenator. Clone $H_1T_2100$ was 1124 bp in size and contained nucleotide 1–1124 sequence which included the entire coding region (sequence encoding the mature ps20 protein). Clone $H_6B_2$-3 was approximately 1000 bp in size and contained the entire 3' untranslated region (including the poly A tail) and the coding sequence (overlap with clone $H_1T_2100$) minus the first few amino acids. The human nucleotide sequence and derived amino acid sequence (the human cDNA sequence encoded a 220 amino acid protein) were compared to the rat ps20 sequences using the MacVector 4.1 sequence analysis program. Based on these analyses, the human and rat amino acid sequences (Positions 1–212, rat) were well conserved in sequence with a 82.1% direct match and a 90.6% overall similarity when considering conservative substitutions of amino acids. The human ps20 protein contains an extra seven amino acids in the amino terminal leader peptide sequence and an added amino acid at position #52.

The nucleotide sequence of human ps20 is shown as Sequence ID No. 3 in FIG. 9. The derived amino acid sequence of human ps20 is shown as Sequence ID No. 4 in FIG. 10.

Many other variations and modifications may be made in the methods herein described, by those having experience in this art, without departing from the concept of the present invention. Accordingly, it should be clearly understood that the methods described in the foregoing description are illustrative only, and not intended as a limitation on the scope of the invention.

What is claimed:

1. An isolated cDNA encoding urogenital sinus derived growth inhibitory factor (ps20), wherein said cDNA comprises the sequence of SEQ ID No. 1.

2. An isolated cDNA encoding urogenital sinus derived growth inhibitory factor (ps20), wherein said cDNA comprises the sequence of SEQ ID No. 3.

3. A DNA that codes for ps20, which DNA has the nucleotide sequence of SEQ ID No. 3.

4. A purified and isolated DNA molecule, wherein said DNA molecule encodes a polypeptide comprising the amino acid sequence of SEQ ID No. 2 or SEQ ID No. 4.

5. A biologically functional vector comprising a DNA molecule comprising the sequence of SEQ ID No. 1.

6. A biologically functional vector comprising a DNA molecule comprising the sequence of SEQ ID No. 3.

7. A biologically functional vector comprising a DNA molecule encoding the amino acid sequence of SEQ ID No. 2 or SEQ ID No. 4.

8. A host cell containing the vector of claim 7.

9. A method of making a recombinant polypeptide comprising expressing an isolated nucleic acid in a host cell, wherein said isolated nucleic acid encodes the amino acid sequence of SEQ ID No. 2 or SEQ ID No. 4.

* * * * *

SEQUENCE LISTING (1) GENERAL INFORMATION:

(iii) NUMBER OF SEQUENCES: 15

(2) INFORMATION FOR SEQ ID NO:1:

(i) SEQUENCE CHARACTERISTICS:
       (A) LENGTH: 1071 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:1:

```
CGGCACGAGG AGGTCACTCG TGCAGAAGGA AAGCCTGCCA CCAGCCTCGG GATGGGTAGC      60
TGCGACAGGA AAGCCCTCTG GGCTCTGAGC TTCCTACTGC TGCTACTGGG CTCCAGCTCT     120
GTTCAGGGCA CTTGGGAGGC AATGTTGCCG GTCAGGCTGG CTGAGAAGTC CCAAGCTGAA     180
GAGGTTGCAG CAACAGGCTC CCGGCAGCCC CACGCAGACC GCTGCCCACC ACCGCCACGG     240
ACGCTACCCC CGGGTGCCTG TCAGGCCACA CGCTGCCAGT CTGACTCTGA GTGCCCACGA     300
CACAGACGCT GCTGTTACAA CGGCTGTGCC TATGCCTGCC TGGAGGCGGT GCCACCGCCA     360
CCAGTTCTAG ACTGGCTGGT GCAGCCCAAA CCACGGTGGC TTGGTGGCAA TGGCTGGCTG     420
CTGGATGGTC CGGAGGAAGT GTTACAAGCA GAGGCCTGCA GCACCACTGA GGATGGGGCA     480
GAGCCACTCC TCTGTCCCTC AGGCTATGAG TGCCACATCC TGCAGCCAGG GGATGCGGCC     540
CAGGGCATAC CCAACCATGG ACGGTGTGTT AAGCAACGTC GACAAGCAGA GGGGCGGGTC     600
CTGCGACAGA AGCTTCACAA GGAGTACCCA GAAGGTGACT CCAAGTATGT GGCAGAGCCT     660
GGGAAGGGAC AACAGAGGCA CTTTCCATGA AGTGGAGACT GGCTGCCTTT GTGGGGCCTT     720
TCCTGTGCTT TCCACACACT ACCCCTTGGA AACAGCAAAA GAATTTGACC CTAGACGTCA     780
AACTCCATTC CACAGAACGG GACTCCAGAG CTCCTGGGAA ACGGGACTTC AGACTCCCAA     840
CCCCAGAGTG GCCCAGCCTG GTGCGGCGGT AACTTGGCGG AAGCCCCTGA CCACCTCTGG     900
GTCCCCGCTC AGCATCCTTG TCACAGGAAC CCGCAGCTTC TAGGTGACTT TGCAGATTTT     960
GCCTGCAGAA GGCATATATT CATCTCTTTT TTTCCCCGAA TAAATCTGCC CACCATGTAG    1020
CAGAAATAAG TTCCTTTATC AGGCTCAAGT CCNAAAAAAA AAAAAAAAA A              1071
```

(2) INFORMATION FOR SEQ ID NO:2:

(i) SEQUENCE CHARACTERISTICS:
       (A) LENGTH: 212 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:2:

```
Met Gly Ser Cys Asp Arg Lys Ala Leu Trp Ala Leu Ser Phe Leu Leu
 1               5                  10                  15

Leu Leu Leu Gly Ser Ser Val Gln Gly Thr Trp Glu Ala Met Leu
            20                  25                  30

Pro Val Arg Leu Ala Glu Lys Ser Gln Ala Glu Glu Val Ala Ala Thr
            35                  40                  45

Gly Ser Arg Gln Pro His Ala Asp Arg Cys Pro Pro Pro Arg Thr
 50                  55                  60
```

```
Leu Pro Pro Gly Ala Cys Gln Ala Thr Arg Cys Gln Ser Asp Ser Glu
 65                  70                  75                  80

Cys Pro Arg His Arg Arg Cys Cys Tyr Asn Gly Cys Ala Tyr Ala Cys
                 85                  90                  95

Leu Glu Ala Val Pro Pro Pro Val Leu Asp Trp Leu Val Gln Pro
            100                 105                 110

Lys Pro Arg Trp Leu Gly Gly Asn Gly Trp Leu Leu Asp Gly Pro Glu
            115                 120                 125

Glu Val Leu Gln Ala Glu Ala Cys Ser Thr Thr Glu Asp Gly Ala Glu
            130                 135                 140

Pro Leu Leu Cys Pro Ser Gly Tyr Glu Cys His Ile Leu Gln Pro Gly
145                 150                 155                 160

Asp Ala Ala Gln Gly Ile Pro Asn His Gly Arg Cys Val Lys Gln Arg
                165                 170                 175

Arg Gln Ala Glu Gly Arg Val Leu Arg Gln Lys Leu His Lys Glu Tyr
            180                 185                 190

Pro Glu Gly Asp Ser Lys Tyr Val Ala Glu Pro Gly Lys Gly Gln Gln
            195                 200                 205

Arg His Phe Pro
    210
```

(2) INFORMATION FOR SEQ ID NO:3:

(i) SEQUENCE CHARACTERISTICS:
        (A) LENGTH: 1366 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

```
GTGCTGGACG CGGACACATG ATCCGAGGGA CCCTGCTGGG TGGAACTAAG AAAGTCCAGC      60

AGACTGTGCA CGCTCCTGTC CCCACTCACA GGCCCACGCA GCGAGGGGGG CCCCTCTTCT     120

GTGTGCGTCT GGAAGGTCGC TGCCCAGGGA GGAAATGCCT TTAACCGGCG TGGGGCCGGG     180

CAGCTGCAGG AGGCAGATCA TCCGGGCTCT GTGCCTCTTG CTACTTCTCC TCCACGCCGG     240

CTCTGCCAAG AATATCTGGA AACGGGCATT GCCTGCGAGG CTGGCCGAGA AATCCCGTGC     300

CGAGGAGGCG GGCGCGCCCG GCGGCCCCCG GCAGCCCCGA GCAGACCGCT GCCCGCCGCC     360

TCCGCGGACG CTGCCCCCCG GCGCCTGCCA GGCCGCGCGC TGTCAGGCGG ACTCCGAGTG     420

CCCGCGGCAC CGGCGCTGCT GCTACAACGG ATGCGCCTAC GCCTGCCTAG AAGCTGTGCC     480

GCCCCCGCCA GTCTTAGACT GGCTGGTGCA GCCGAAACCT CGATGGCTTG GTGGCAATGG     540

CTGGCTCCTG GATGGCCCTG AGGAGGTGTT ACAAGCAGAG GCGTGCAGCA CCACGGAGGA     600

TGGGGCCGAA CCCCTGCTCT GTCCCTCGGG CTATGAGTGC CACATCCTGA GCCCAGGTGA     660

CGTGGCCGAA GGTATCCCCA ACCGTGGGCA GTGCGTCAAG CAGCGCCGGC AAGCAGATGG     720

GCGAATCCTA CGACACAAAC TTTACAAAGA ATATCCAGAA GGTGACTCAA AGAATGTGGC     780

AGAACCTGGA AGGGACAAC AGAGGCACTT TCAGTAAAGC AACGGCAAGC AGCTAGGTTG     840

CAAGAACATT CCTCTACTTT CTGCTAAGCC TTGGAAACAG TTGGGAAAAG TAGTTTGACC     900

CTCACAGTTC ACATTCAGCT CAGCAGAGCA AGACCCCAGA GATGCTTAGA GACAGGACAC     960

CTGGCCATCA AACCCAGTTT GGCCCAGCCT GGTTGGGTGA CTTTGTGGGA GCCACTTAAC    1020

AGCTCTGGGT CCCTGTTTTA CCATCCTGGG AGCAAGGCCC TGCAGCTCCA CGAGACCTTT    1080
```

```
ACCCCGGGAA GAAGCCGCCG CCCATGAAAG CATTTCTGAA GCCCCTTTCT AAGACAAGGC    1140

TCAGCATCTT GATATTTTTG ACAGATTCCT CCCAAGTCTG GCTCTGGGAG GTATGTACCC    1200

ATCTCAAATG TTCCCAAGAT AAATTCATCC TTCAGGAAAT GGAAATGAAC TTGCTTACTA    1260

ATGTGTGATT CCTAGTTGTA GCCACCGGAT GTGCTGAGGC CTAAATGTTA GCAGGTGGGA    1320

GGAGGCCACA GAACAATAAA AACAACCAAA TAAAAAAAAA AAAAAA                   1366
```

(2) INFORMATION FOR SEQ ID NO:4:

(i) SEQUENCE CHARACTERISTICS:
        (A) LENGTH: 220 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

```
Met Pro Leu Thr Gly Val Gly Pro Gly Ser Cys Arg Arg Gln Ile Ile
  1               5                  10                  15

Arg Ala Leu Cys Leu Leu Leu Leu Leu His Ala Gly Ser Ala Lys
             20                  25                  30

Asn Ile Trp Lys Arg Ala Leu Pro Ala Arg Leu Ala Glu Lys Ser Arg
             35                  40                  45

Ala Glu Glu Ala Gly Ala Pro Gly Gly Pro Arg Gln Pro Arg Ala Asp
 50                  55                  60

Arg Cys Pro Pro Pro Arg Thr Leu Pro Pro Gly Ala Cys Gln Ala
 65                  70                  75                  80

Ala Arg Cys Gln Ala Asp Ser Glu Cys Pro Arg His Arg Arg Cys Cys
                 85                  90                  95

Tyr Asn Gly Cys Ala Tyr Ala Cys Leu Glu Ala Val Pro Pro Pro
                100                 105                 110

Val Leu Asp Trp Leu Val Gln Pro Lys Pro Arg Trp Leu Gly Gly Asn
                115                 120                 125

Gly Trp Leu Leu Asp Gly Pro Glu Glu Val Leu Gln Ala Glu Ala Cys
130                 135                 140

Ser Thr Thr Glu Asp Gly Ala Glu Pro Leu Leu Cys Pro Ser Gly Tyr
145                 150                 155                 160

Glu Cys His Ile Leu Ser Pro Gly Asp Val Ala Glu Gly Ile Pro Asn
                165                 170                 175

Arg Gly Gln Cys Val Lys Gln Arg Gln Ala Asp Gly Arg Ile Leu
                180                 185                 190

Arg His Lys Leu Tyr Lys Glu Tyr Pro Glu Gly Asp Ser Lys Asn Val
                195                 200                 205

Ala Glu Pro Gly Arg Gly Gln Gln Arg His Phe Gln
210                 215                 220
```

(2) INFORMATION FOR SEQ ID NO:5:

(i) SEQUENCE CHARACTERISTICS:
        (A) LENGTH: 1042 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

```
CGGCACGAGG AGGTCACTCG TGCAGAAGGA AAGCCTGCCA CCAGCCTCGG GATGGGTAGC    60
```

```
TGCGACAGGA AAGCCCTCTG GGCTCTGAGC TTCCTACTGC TGCTACTGGG CTCCAGCTCT    120

GTTCAGGGCA CTTGGGAGGC AATGTTGCCG GTCAGGCTGG CTGAGAAGTC CCAAGCTGAA    180

GAGGTTGCAG CAACAGGCTC CCGGCAGCCC CACGCAGACC GCTGCCCACC ACCGCCACGG    240

ACGCTACCCC CGGGTGCCTG TCAGGCCACA CGCTGCCAGT CTGACTCTGA GTGCCCACGA    300

CACAGACGCT GCTGTTACAA CGGCTGTGCC TATGCCTGCC TGGAGGCGGT GCCACCGCCA    360

CCAGTTCTAG ACTGGCTGGT GCAGCCCAAA CCACGGTGGC TTGGTGGCAA TGGCTGGCTG    420

CTGGATGGTC CGGAGGAAGT GTTACAAGCA GAGGCCTGCA GCACCACTGA GGATGGGGCA    480

GAGCCACTCC TCTGTCCCTC AGGCTATGAG TGCCACATCC TGCAGCCAGG GGATGCGGCC    540

CAGGGCATAC CCAACCATGG ACGGTGTGTT AAGCAACGTC GACAAGCAGA GGGGCGGGTC    600

CTGCGACAGA AGCTTCACAA GGAGTACCCA GAAGGTGACT CCAAGTATGT GGCAGAGCCT    660

GGGAAGGGAC AACAGAGGCA CTTTCCATGA AGTGGAGACT GGCTGCCTTT GTGGGCCTT    720

TCCTGTGCTT TCCACACACT ACCCCTTGGA AACAGCAAAA GAATTTGACC CTAGACGTCA    780

AACTCCATTC CACAGAACGG GACTCCAGAG CTCCTGGGAA ACGGGACTTC AGACTCCCAA    840

CCCCAGAGTG GCCCAGCCTG GTGCGGCGGT AACTTGGCGG AAGCCCCTGA CCACCTCTGG    900

GTCCCCGCTC AGCATCCTTG TCACAGGAAC CCGCAGCTTC TAGGTGACTT TTGCAGATTT    960

TGCCTGCAGA AGGCATATAT TCATCTCTTT TTTTCCCCGA ATAAATCTGC CCACCATGTA    1020

GCAGAAATTA AAAAAAAAA AA                                             1042
```

(2) INFORMATION FOR SEQ ID NO:6:

(i) SEQUENCE CHARACTERISTICS:
        (A) LENGTH: 212 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:6:

```
Met Gly Ser Cys Asp Arg Lys Ala Leu Trp Ala Leu Ser Phe Leu Leu
 1               5                  10                  15

Leu Leu Leu Gly Ser Ser Ser Val Gln Gly Thr Trp Glu Ala Met Leu
            20                  25                  30

Pro Val Arg Leu Ala Glu Lys Ser Gln Ala Glu Val Ala Ala Thr
        35                  40                  45

Gly Ser Arg Gln Pro His Ala Asp Arg Cys Pro Pro Pro Arg Thr
50                  55                  60

Leu Pro Pro Gly Ala Cys Gln Ala Thr Arg Cys Gln Ser Asp Ser Glu
65                  70                  75                  80

Cys Pro Arg His Arg Arg Cys Cys Tyr Asn Gly Cys Ala Tyr Ala Cys
                85                  90                  95

Leu Glu Ala Val Pro Pro Pro Val Leu Asp Trp Leu Val Gln Pro
                100                 105                 110

Lys Pro Arg Trp Leu Gly Gly Asn Gly Trp Leu Leu Asp Gly Pro Glu
            115                 120                 125

Glu Val Leu Gln Ala Glu Ala Cys Ser Thr Thr Glu Asp Gly Ala Glu
        130                 135                 140

Pro Leu Leu Cys Pro Ser Gly Tyr Glu Cys His Ile Leu Gln Pro Gly
145                 150                 155                 160

Asp Ala Ala Gln Gly Ile Pro Asn His Gly Arg Cys Val Lys Gln Arg
                165                 170                 175
```

```
Arg Gln Ala Glu Gly Arg Val Leu Arg Gln Lys Leu His Lys Glu Tyr
            180                 185                 190

Pro Glu Gly Asp Ser Lys Tyr Val Ala Glu Pro Gly Lys Gly Gln Gln
        195                 200                 205

Arg His Phe Pro
    210
```

(2) INFORMATION FOR SEQ ID NO:7:

(i) SEQUENCE CHARACTERISTICS:
        (A) LENGTH: 48 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

```
Cys Pro Pro Pro Arg Thr Leu Pro Pro Gly Ala Cys Gln Ala Thr
 1               5                  10                  15

Arg Cys Gln Ser Asp Ser Glu Cys Pro Arg His Arg Arg Cys Cys Tyr
            20                  25                  30

Asn Gly Cys Ala Tyr Ala Cys Leu Glu Ala Val Pro Pro Pro Val
            35                  40                  45
```

(2) INFORMATION FOR SEQ ID NO:8:

(i) SEQUENCE CHARACTERISTICS:
        (A) LENGTH: 44 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:8:

```
Cys Pro Pro Lys Lys Ser Ala Gln Cys Leu Arg Tyr Lys Lys Pro Glu
 1               5                  10                  15

Cys Gln Ser Asp Trp Gln Cys Pro Gly Lys Lys Arg Cys Cys Pro Asp
            20                  25                  30

Thr Cys Gly Ile Lys Cys Leu Asp Pro Val Thr Pro
            35                  40
```

(2) INFORMATION FOR SEQ ID NO:9:

(i) SEQUENCE CHARACTERISTICS:
        (A) LENGTH: 42 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:9:

```
Cys Pro Arg Val Met Ile Tyr Cys Pro Ala Arg His Pro Asn Lys
 1               5                  10                  15

Cys Thr Ser Asp Tyr Asp Cys Pro Lys Pro Gln Lys Cys Cys Pro Gly
            20                  25                  30

Tyr Cys Gly Lys Gln Cys Tyr Gln Pro Glu
            35                  40
```

(2) INFORMATION FOR SEQ ID NO:10:

(i) SEQUENCE CHARACTERISTICS:
        (A) LENGTH: 42 amino acids

```
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:10:

Cys Pro Ile Ile Leu Ile Arg Cys Ala Met Leu Asn Pro Pro Asn Arg
 1               5                  10                  15

Cys Leu Lys Asp Thr Asp Cys Pro Gly Ile Lys Lys Cys Cys Glu Gly
             20                  25                  30

Ser Cys Gly Met Ala Cys Phe Val Pro Gln
         35                  40

(2) INFORMATION FOR SEQ ID NO:11:

(i) SEQUENCE CHARACTERISTICS:
            (A) LENGTH: 38 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:11:

Cys Pro Glu Leu Gln Ala Asp Gln Asn Cys Thr Gln Glu Cys Val Ser
 1               5                  10                  15

Asp Ser Glu Cys Ala Asp Asn Leu Lys Cys Cys Ser Ala Gly Cys Ala
             20                  25                  30

Thr Phe Cys Pro Asn Asp
         35

(2) INFORMATION FOR SEQ ID NO:12:

(i) SEQUENCE CHARACTERISTICS:
            (A) LENGTH: 44 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:12:

Cys Pro Lys Thr Ser Gly Pro Gly Ile Cys Leu His Gly Cys Asp Ser
 1               5                  10                  15

Asp Ser Asp Cys Lys Glu Gly Gln Lys Cys Cys Phe Asp Gly Cys Gly
             20                  25                  30

Tyr Ile Cys Leu Thr Val Ala Pro Ser Gly Ser Pro
         35                  40

(2) INFORMATION FOR SEQ ID NO:13:

(i) SEQUENCE CHARACTERISTICS:
            (A) LENGTH: 43 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:13:

Cys Pro Ala Pro Glu Lys Ala Ser Gly Phe Ala Ala Ala Cys Val Glu
 1               5                  10                  15

Ser Cys Glu Val Asp Asn Glu Cys Ser Gly Val Lys Lys Cys Cys Ser
             20                  25                  30
```

```
Asn Gly Cys Gly His Thr Cys Gln Val Pro Lys
        35                  40
```

(2) INFORMATION FOR SEQ ID NO:14:

(i) SEQUENCE CHARACTERISTICS:
        (A) LENGTH: 51 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:14:

```
Cys Pro Trp Asn Pro Ile Gln Met Ile Ala Ala Gly Pro Cys Pro Lys
1               5                   10                  15

Asp Asn Pro Cys Ser Ile Asp Ser Asp Cys Ser Gly Thr Met Lys Cys
            20                  25                  30

Cys Lys Asn Gly Cys Ile Met Ser Cys Met Asp Pro Glu Pro Lys Ser
        35                  40                  45

Pro Thr Val
    50
```

(2) INFORMATION FOR SEQ ID NO:15:

(i) SEQUENCE CHARACTERISTICS:
        (A) LENGTH: 42 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:15:

```
Cys Pro Lys Asn Pro Pro Arg Ser Ile Gly Thr Cys Val Glu Leu Cys
1               5                   10                  15

Ser Gly Asp Gln Ser Cys Pro Asn Ile Gln Lys Cys Cys Ser Asn Gly
            20                  25                  30

Cys Gly His Val Cys Lys Ser Pro Val Phe
        35                  40
```